United States Patent [19]

Hooper et al.

[11] 4,289,641

[45] Sep. 15, 1981

[54] DETERGENT PRODUCT

[75] Inventors: David C. Hooper, Ashford; George A. Johnson; Donald Peter, both of Wirral, all of England

[73] Assignee: Lever Brothers Company, New York, N.Y.

[21] Appl. No.: 933,931

[22] Filed: Aug. 15, 1978

[30] Foreign Application Priority Data

Jan. 12, 1978 [GB] United Kingdom ................ 1285/78

[51] Int. Cl.$^3$ .......................... C11D 9/44; C11D 9/50
[52] U.S. Cl. ...................................... 252/96; 252/97; 252/108; 252/109; 252/132; 252/174.12; 252/522 R
[58] Field of Search ...................... 252/108, 97, 99, 94, 252/107, 96, 109, 121, 132, 135, 522, 174.12; 424/65

[56] References Cited

U.S. PATENT DOCUMENTS

| | | | |
|---|---|---|---|
| 2,875,131 | 2/1959 | Carpenter et al. | 252/522 X |
| 2,889,254 | 6/1959 | Fiore et al. | 252/522 X |
| 2,976,321 | 3/1961 | Dorsky et al. | 252/522 X |
| 3,144,467 | 8/1964 | Houlihan | 260/343.2 |
| 3,268,594 | 8/1966 | Bedoukian | 260/615 |
| 3,317,397 | 5/1967 | Saunders | 252/108 X |
| 3,318,945 | 5/1967 | Erman | 260/468 |
| 3,493,650 | 2/1970 | Dunkel | 424/65 |
| 3,591,643 | 7/1971 | Fanta et al. | 260/617 F |
| 3,662,007 | 5/1972 | Fanta et al. | 260/631.5 |
| 3,679,756 | 7/1972 | Kretschmar et al. | 260/631.5 |
| 3,684,723 | 8/1972 | Best et al. | 252/132 |
| 3,836,232 | 10/1974 | Ohloff et al. | 252/522 |
| 3,862,049 | 1/1975 | McGarth et al. | 252/108 |
| 3,969,259 | 7/1976 | Lages | 252/107 |
| 4,055,506 | 10/1977 | Pittet et al. | 252/132 |
| 4,066,710 | 1/1978 | Ochsner | 260/631.5 |
| 4,100,110 | 7/1978 | Ansari et al. | 252/522 |
| 4,129,569 | 12/1978 | Schreiber et al. | 260/307 FA |
| 4,131,557 | 12/1978 | Hall et al. | 252/132 |

FOREIGN PATENT DOCUMENTS

| | | |
|---|---|---|
| 2440025 | 3/1975 | Fed. Rep. of Germany . |
| 2454969 | 5/1975 | Fed. Rep. of Germany . |
| 2461593 | 7/1975 | Fed. Rep. of Germany . |
| 2502767 | 7/1975 | Fed. Rep. of Germany . |
| 2535576 | 2/1976 | Fed. Rep. of Germany . |
| 2540624 | 4/1976 | Fed. Rep. of Germany . |
| 2455761 | 6/1976 | Fed. Rep. of Germany . |
| 2461605 | 10/1976 | Fed. Rep. of Germany . |

OTHER PUBLICATIONS

"Handbuch der Kosmetika and Riechstoffe, Band 2", H. Janistyn, 1969.
"Hanbuch der Gesamten Parfumerie and Kosmetik," Fred Winter, 1952, pp. 735-754.
Sagarin, "Cosmetics-Science & Technology" (M. S. Balsam), Chapter 32, 1972, pp. 599 and 608-621.

*Primary Examiner*—P. E. Willis, Jr.
*Attorney, Agent, or Firm*—James J. Farrell; Melvin H. Kurtz; Irving N. Feit

[57] ABSTRACT

A deodorant detergent product comprises a soap; detergent adjuncts including a detergency builder (other than soap) and/or a bleach; and a deodorant composition. The product can be employed for washing fabrics which when subsequently worn in contact with the skin aid in the reduction of human body malodor.

14 Claims, No Drawings

DETERGENT PRODUCT

This invention relates to deodorant detergent products for use in suppressing human body malodour.

BACKGROUND TO THE INVENTION

It has long been recognised that the development of body malodour is largely due to bacterial action on the products of the sweat glands. Washing the skin with a detergent, for instance in the form of a personal washing detergent bar, removes malodorous products and reduces the concentration of bacteria on the skin. Likewise, washing soiled clothing with a fabric washing detergent product, for instance in the form of a powder or liquid detergent product, removes malodorous products and bacteria derived from the skin.

It has been customary to incorporate germicides into detergent products, particularly those designed for personal washing, in the belief that growth of those skin microflora that contribute to body malodour can be inhibited and the production of malodorous substances suppressed. Germicides are at least partly effective in reducing or retarding the development of body malodour, but they do not completely solve the problem, possibly because there are other causes of malodour development on the skin which are unrelated to the proliferation of bacteria.

SUMMARY OF THE INVENTION

It has now been discovered that certain combinations of materials other than germicides, hereinafter referred to as "deodorant compositions", when incorporated into a fabric washing detergent product, can be deposited onto the fabric of a garment washed with the product, so that the fabric of the garment then has the property of reducing body malodour when the garment is subsequently worn in contact with the skin.

In the course of attempts to characterise this new principle, many hundreds of materials have been screened. Furthermore, detergent products containing hundreds of formulations made by blending materials have been examined in order to characterise the new principle.

DEFINITION OF THE INVENTION

In its widest aspect, the invention provides a deodorant detergent product comprising from 1 to 99% by weight of a soap, from 0.99 to 98.99% by weight of other detergent adjuncts including at least one chosen from detergency builders (other than soap) and bleaches, and from 0.01 to 10% by weight of a deodorant composition comprising from 45 to 100% by weight of deodorant components, said components having a lipoxidase-inhibiting capacity of at least 50% or a Raoult Variance Ratio of at least 1.1, said components being classified into six classes consisting of:
Class 1: phenolic substances
Class 2: essential oils, extracts, resins and synthetic oils
Class 3: aldehydes and ketones
Class 4: polycyclic compounds
Class 5: esters
Class 6: alcohols provided that where a component can be classified into more than one class it is placed in the lower or lowest numbered class; said components being selected so that:

(a) the deodorant composition contains at least five components of which at least one must be selected from each of class 1, class 2 and class 4;

(b) the deodorant composition contains components from at least 4 of the 6 classes; and (c) any component present in the deodorant composition at a concentration of less than 0.5% by weight of said composition is eliminated from the requirements of (a) and (b).

The invention also provides a process for preparing a deodorant detergent product which process comprises blending a soap, other detergent adjuncts including at least one chosen from detergency builders (other than soap) and bleaches and a deodorant composition as herein defined to provide a deodorant detergent product.

The invention furthermore provides a method for suppressing human body malodour which comprises contacting the skin with a fabric treated with a deodorant detergent product as herein defined.

It is a preferred property of the deodorant detergent product of the invention that it should comprise a deodorant composition which satisfies a deodorancy test when applied to the skin of human subjects. The average amount by which body malodour should be reduced is expressed in terms of the deodorant value of the deodorant composition contained in the detergent product. Products of the invention accordingly preferably comprise a deodorant composition having a deodorant value of from 0.50 to 3.5. Products in which the deodorant composition has a deodorant value of below 0.50 are outside the scope of this invention and are considered to be incapable of reducing body malodour to a significant extent.

The Deodorant Value Test

In this test the deodorant value of a deodorant composition is measured by assessing its effectiveness, when contained in a standard soap bar at a standard concentration, in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base employed in many of the tests referred to later in this specification is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and plodded in conventional equipment, cut into billets and stamped into bars. The deodorant composition to be tested is therefore present at the standard level of 1.5%. These bars are described as 80/20/5 soap base and consist of 80 parts tallow soap and 20 parts coconut soap, 5 parts of this soap mixture being free fatty acids expressed as coconut oil fatty acid.

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include anti-oxidants in the control bar, but these should be present only in the amount required to stabilise the soap base.

The test is conducted as follows:

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the procedure described in Whitehouse and Carter, Proc. Scientific Section of the Toilet Goods Association, 48, 31, (1967).

A panel of 50 human subjects for use in the test is assembled from Caucasian male subjects of age within the range of from 20 to 55 years. By screening, subjects are chosen who develop axilliary body malodour that is not unusually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour on a scale from 0 to 5, with 0 corresponding to no odour and 5 representing very strong odour. Before evaluation each subject stands with his arms against his side; he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in Table 1 below.

TABLE 1

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average scope of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

More generally, deodorant values can be determined at other deodorant composition concentrations or with detergent products other than the standard soap bar using a test similar to the test described above. Later in this specification examples are given of powdered and liquid soap products containing other detergent adjuncts as herein defined.

Although the invention in its widest aspect provides deodorant detergent products comprising deodorant compositions having a deodorant value of from 0.50 to 3.5, preferred deodorant detergent products are those comprising deodorant compositions which have a deodorant value of at least 0.60, or 0.70, or 0.80, or 0.90, or 1.00, or 1.20, the higher the minimum value, the more effective is the product as a deodorant detergent product as recorded by the assessors in the deodorant value test. It has also been noted that consumers, who are not trained assessors, can detect by self-assessment a noticeable reduction in body malodour where the deodorant value is at least 0.70, the higher the deodorant value above this figure, the more noticeable is the deodorant effect.

Detergent Active Compound

The product will contain a soap which is a water-soluble or water-dispersible alkali metal salt of an organic acid, especially a sodium or a potassium salt, or the corresponding ammonium or substituted ammonium salt. Examples of suitable organic acids are natural or synthetic aliphatic carboxylic acids of from 10 to 22 carbon atoms, especially the fatty acids of triglyceride oils such as tallow and coconut oil.

The preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantly $C_{14}$ and $C_{18}$ fatty acids, the nut oil fatty acids are of shorter chain length and are predominantly $C_{10}$–$C_{14}$ fatty acids.

The amount of soap that can be incorporated into the deodorant detergent product according to the invention is from 1% to 99% by weight.

The product can also optionally contain non-soap detergents which can be non-soap anionic or nonionic or cationic or amphoteric or Zwitterionic in character. Typical non-soap anionic detergent-active compounds include water-soluble salts, particularly the alkali metal, ammonium and alkanolammonium salts, of organic sulphuric reaction products having in their molecular structure and alkyl group containing from about 8 to about 22 carbon atoms and a sulphonic acid or sulphuric acid ester group. (Included in the term "alkyl" is the alkyl portion of acyl groups). Examples of this group of non-soap detergents which can be used are the sodium and potassium alkyl sulphates, especially those obtained by sulphating the higher alcohols ($C_8$–$C_{18}$ carbon atoms) produced by reducing the glycerides of tallow or coconut oil; and sodium and potassium alkyl benzene sulphonates, in which the alkyl group contains from about 9 to about 15 carbon atoms in straight chain or branched chain configuration.

Other anionic detergent-active compounds include the sodium alkyl glycerol ether sulphonates, especially those ethers of higher alcohols derived from tallow and coconut oil; sodium coconut oil fatty acid monoglyceride sulphonates and sulphates; and sodium or potassium salts of alkyl phenol ethylene oxide ether sulphate containing about 1 to about 10 units of ethylene oxide per molecule and wherein the alkyl groups contain about 8 to about 12 carbon atoms.

Other useful non-soap anionic detergent-active compounds include the water-soluble salts of esters of α-sulphonated fatty acids containing from about 6 to about 20 carbon atoms in the ester group; water-soluble salts of 2-acyloxy-alkane-1-sulphonic acids containing from about 2 to 9 carbon atoms in the acyl group and from about 9 to about 23 carbon atoms in the alkane moiety; alkyl ether sulphates containing from about 10 to 20 carbon atoms in the alkyl group and from about 1 to 30 moles of ethylene oxide; water-soluble salts of olefin sulphonates containing from about 12 to 24 carbon atoms; and 6-alkyloxy alkane sulphonates containing from about 1 to 3 carbon atoms in the alkyl group and from about 8 to 20 carbon atoms in the alkane moiety.

Preferred water-soluble non-soap anionic detergent-active compounds include linear alkyl benzene sulphonates containing from about 11 to 14 carbon atoms in the alkyl group: the tallow range ($C_{12-20}$) alkyl sulphates; the coconut range alkyl glyceryl sulphonates; and alkyl ether sulphates wherein the alkyl moiety contains from about 14 to 18 carbon atoms and wherein the average degree of ethoxylation varies between 1 and 6.

Specific preferred non-soap anionic detergent-active compounds include: sodium linear $C_{10}$–$C_{12}$ alkyl benzene sulphonate; triethanolamine $C_{10}$–$C_{12}$ alkyl benzene sulphonate; sodium tallow alkylsulphate; and sodium coconut alkyl glyceryl ether sulphonate; and the sodium salt of a sulphated condensation product of tallow alcohol with from about 3 to about 10 moles of ethylene oxide.

It is to be understood that any of the foregoing optional anionic detergent-active compounds can be used separately or as mixtures.

Examples of suitable nonionic detergent-active compounds are condensates of linear and branched-chain aliphatic alcohols or carboxylic acids of from 8 to 18 carbon atoms with ethylene oxide, for instance a coconut alcohol-ethylene oxide condensate of 6 to 30 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensates containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide.

Suitable cationic detergent-active compounds are quaternary ammonium salts having an aliphatic radical of from 8 to 18 carbon atoms, for instance cetyltrimethyl-ammonium bromide.

Examples of suitable amphoteric detergent-active compounds are derivatives of aliphatic secondary and tertiary amines containing an alkyl group of 8 to 18 carbon atoms and an aliphatic radical substituted by an anionic water-solubilising group, for instance sodium 3-dodecylaminopropionate, sodium 3-dodecylaminopropane sulphonate and sodium N-2-hydroxydodecyl-N-methyltaurate.

Suitable zwitterionic detergent-active compounds are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N,N-dimethyl-N-hexadecylammonium) propane-1-sulphonate betaine, 3-(dodecylmethyl sulphonium) propane-1-sulphonate betaine and 3-(cetylmethylphosphonium) ethane sulphonate betaine.

Further examples of optional detergent-active compounds are compounds commonly used as surface-active agents given in the well-known textbooks "Surface Active Agents", Volume 1 by Schwartz and Perry and "Surface Active Agents and Detergents", Volume II by Schwartz, Perry and Berch.

The total amount of soap and other optional detergent-active compounds that can be incorporated into deodorant detergent products according to the invention is from about 1% to 98.99% by weight. The preferred amount will depend on the nature of the product (i.e. whether it is liquid or solid and whether it comprises soap or both soap and non-soap detergents).

It can be stated generally that the preferred amount of soap together with optional detergent active compounds to be employed is within the range of from about 5 to about 95% by weight of the product.

The Deodorant Composition

The characterisation of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

The Lipoxidase Test

In this test the capacity of a material to inhibit the oxidation of linoleic acid by lipoxidase (EC1.13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipxodase in the borate buffer and having an activity within the range of from 15,000 to 40,000 units per ml is prepared.

The activity of the lipxodiase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta OD$) at 234 nm within the range of from 0.6 to 1.0 units per minute. The following ingredients are placed in two 3 ml cuvettes:

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100(S_1-S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

The Morpholine Test

In this test the capacity of a material to depress the partial vapour pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g); and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No 2, 87-91 (1972) and by Jentzsch et al in "Z. Anal. Chem." 236, 96-118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1-A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure $(p-p')/p$, is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1-A'/A}{87/(87+m/4)}$$

The above ratio, which will be referred to as the Raoult variance ratio, is calculated from the test results.

Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g. coumarin (natural or synthetic), iso-eugenol, benzyl salicylate. The majority of components are in this category.

(2) Synthetic reaction products (products of reaction), mixtures of isomers and possibly homologues, e.g. α-iso-methyl ionone.

(3) Natural oils, gums and resins, and their extracts, e.g. patchouli oil, geranium oil, clove leaf oil, benzoin resinoid.

(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the detergent product of the invention to use components that, as well as satisfying the lipoxidase or morpholine tests, satisfy further conditions. These conditions are:

(i) there must be at least five components present,
(ii) each of these components must be selected from at least four different chemical classes (to be defined below),
(iii) a component from each of classes 1,2 and 4 must be present,
(iv) at least 45%, preferably at least 50 and most preferably from 60 to 100%, by weight of the deodorant composition must comprise components,
(v) a component is not considered to contribute to the efficacy of the deodorant composition if it is present in the deodorant composition at a concentration of less than 0.5% by weight, and
(vi) a class is not considered to contribute to the efficacy of the deodorant composition if it is present in the deodorant composition at a concentration of less than 0.5% by weight.

Therefore, according to a preferred embodiment of the invention, there is provided a deodorant detergent product as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range 0.50 to 3.5.

Each component should be allocated to one of six classes. These classes are:
Class 1—Phenolic substances
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume & Flavour Materials of Natural Origin" (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

| Class 1 - Phenolic Substances | | | |
|---|---|---|---|
| | LIC | RVR | m |
| iso-Amyl salicylate | 95 | 1.24 | 208 |
| Benzyl salicylate | 0 | 1.58 | 226 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |

| Class 2 - Essential oils, extracts, resins, "synthetic" oils. (denoted by "AB") | | | |
|---|---|---|---|
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |

| Class 3 - Aldehydes and Ketones | | | |
|---|---|---|---|
|  | LIC | RVR | m |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl naphthyl ketone | 100 | 0.96 | 170 |

| Class 4 - Polycyclic Compounds | | | |
|---|---|---|---|
|  | LIC | RVR | m |
| Coumarin | 58 | 1.22 | 146 |
| 1,3,4,6,7,8-Hexahydro-4,6,6,7,8,8-hexamethyl cyclopenta-γ-2-benzo-pyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |

| Class 5 - Esters | | | |
|---|---|---|---|
|  | LIC | RVR | m |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |

| Class 6 - Alcohols | | | |
|---|---|---|---|
|  | LIC | RVR | m |
| Dimyrcetol | 16 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present; the lower the minimum concentration. The minimum average concentration in the various situations that can apply is shown in the Table below:

| Number of classes represented in deodorant composition | Average concentration of components | |
|---|---|---|
|  | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant detergent product as herein defined wherein the amount of deodorant components in the deodorant composition present in the classes 1,2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant detergent product for purposes other than obtaining deodorant effects, for example an adjunct like the anti-oxidant, are excluded from the operation of the preceding instructions to the extent that the component is required for that other purpose. The levels at which adjuncts are conventionally present in detergent products is well-established for established materials and readily determinable for new materials so that the application of the above exclusion presents no difficulty.

Deodorant compositions can be incorporated in deodorant detergent products according to the invention, at a concentration of from about 0.01 to about 10%, preferably from 0.5 to 5% and most preferably from 1 to 3% by weight.

It is apparent that if less than 0.01% of a deodorant composition is employed, then use of the detergent product is unlikely to provide a significant reduction in body malodour intensity. If more than 10% of a deodorant composition is employed, then use of the detergent product is unlikely to further reduce body malodour intensity beyond that observed at the 10% level.

Detergent Adjuncts

Deodorant detergent products of the invention contain other detergent composition ingredients (adjuncts), which will include at least one adjunct chosen from detergency builders (other than soap) and bleaches.

Detergency Builders other than Soap

Useful builders include inorganic and organic water-soluble builder salts, as well as various water-insoluble and so-called "seeded" builders.

Inorganic detergency builders include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates and hexametaphosphates. The polyphosphonates specifically include, for example, the sodium and potassium salts of ethylene diphosphonic acid, the sodium and potassium salts of ethane 1-hydroxy-1,1-diphosphic acid, and the sodium and potassium salts of ethane-1,1,2-triphosphonic acid. Sodium tripolyphosphate is an especially preferred, water-soluble inorganic builder.

Non-phosphorous containing sequestrants can also be selected for use as detergency builders. Specific examples of non-phosphorus, inorganic builder ingredients include water-soluble inorganic carbonate, bicarbonate, borate and silicate salts. The alkali metal, e.g. sodium and potassium, carbonates, bicarbonates, borates (Borax) and silicates are particularly useful.

Water-soluble, non-phosphorous organic builders are also useful. For example, the alkali metal, ammonium and substituted ammonium polyacetates, carboxylates, polycarboxylates, succinates, and polyhydroxysulphonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builder materials (both organic and inorganic) include sodium carbonate, sodium bicarbonate, sodium silicate, sodium citrate, sodium oxydisuccinate, sodium mellitate, sodium nitrilotriacetate, and sodium ethylenediaminetetraacetate, carboxymethoxysuccinate, carboxymethoxymalonate and mixtures thereof.

Another type of detergency builder material useful in the products of the invention comprises a water-soluble material capable of forming a water-insoluble reaction product with water hardness cations in combination with a crystallization seed which is capable of providing growth sites for said reaction product.

Specific examples of materials capable of forming the water-insoluble reaction product include the water-soluble salts of carbonates, bicarbonates, sequicarbonates, silicates, aluminates and oxalates. The alkali metal, especially sodium salts of the foregoing materials are preferred for convenience and economy.

Another type of builder useful herein includes various substantially water-insoluble materials which are capable of reducing the hardness content of laundering liquors, e.g. by ion-exchange processes.

The complex aluminosilicates, i.e zeolite-type materials, are useful presoaking/washing adjuvants in that these materials soften water, i.e. remove $Ca^{++}$ hardness. Both the naturally occurring and synthetic "zeolites", especially zeolite A and hydrated zeolite A materials, are useful for this builder purpose.

The detergency builder component when present will generally comprise from about 1% to 90%, preferably from about 5% to 75% by weight of the product.

Bleaches

Useful bleaches include, for example, the various organic peroxyacids such as peracetic acid, peradipic acid, perphthalic acid, diperphthalic acid, diperisophthalic acid, diperazelaic acid and the like. Inorganic bleaches, i.e. persalts including such materials as sodium perborate, sodium perborate tetra-hydrate, urea peroxide, and the like, can be employed in the compositions. Bleach precursors such as tetraacetyl ethylene diamine and sodium acetoxybenzoyl sulphonate can also be employed. Bleaches or their precursors when employed can be used at a level of from about 1% to 45% by weight of the composition.

An especially preferred bleaching agent is sodium perborate tetrahydrate, at an effective concentration of from about 10% to about 40% by weight of the product.

If necessary, bleach stabilisers such as magnesium sulphate can also be included together with a bleach.

Other Detergent Adjuncts

Other detergent adjuncts that can optionally be present in the product include sequestrants, superfatting agents, such as free long-chain fatty acids, lather boosters, such as coconut monoethanolamide; lather controllers; inorganic salts such as sodium and magnesium sulphates; moisturisers; plasticisers and anti-caking agents; antiredeposition agents; soil release agents; filler materials; optical brighteners; anti-spotting agents; dyes; thickeners; opacifiers, colourants, fluorescers, perfumes, germicides and other deodorant materials such as zinc ricinoleate; and water.

Various detergency enzymes well-known in the art for their ability to degrade and aid in the removal of various soils and stains can also optionally be employed in products according to this invention. Detergency enzymes are commonly used at concentrations of from about 0.1% to about 1.0% by weight of such compositions. Typical enzymes include the various proteases, lipases, amylases, and mixtures thereof, which are designed to remove a variety of soils and stains from fabrics.

The total amount of detergent adjuncts that can be incorporated into the deodorant detergent product according to the invention will normally form the balance of the product after accounting for the deodorant perfume and the detergent-active compound. The detergent adjunct will accordingly form from 0.99% to 98.99% by weight of the product.

Product Types and Formulations

The deodorant detergent product can be formulated as a solid product, for example in the form of a laundry bar or a powder which can be used for fabric washing. Alternatively, the product can take the form of a liquid product for fabric washing. As a further alternative, the composition can take the form of a gelled product for fabric washing.

It is to be understood that the foregoing products are examples of forms which the deodorant detergent product can take; other product forms within the purview of the art are to be included within the scope of monopoly claimed.

Preparation of Deodorant Detergent Products

The deodorant detergent products of the invention as intended for fabric washing can be prepared as liquid products or as solid products, for example in the form of a bar or a powder.

Liquid products can be prepared simply by mixing the ingredients in any desired order, although it is preferable to add any volatile components which can include the deodorant composition towards the end of the mixing process to limit loss by evaporation of these volatile components. Some agitation is usually necessary to ensure proper dispersion of any insoluble ingredients and proper dissolution of soluble ingredients.

Solid products in the form of a powder can be prepared by first making a slurry with water of all ingredients of the composition except those which are heat labile, volatile or otherwise unstable to heating, for example the deodorant composition and bleach ingredients.

By way of example, a typical slurry will have the following composition:

|  | % w/w |
|---|---|
| Detergent active(s) | 17 |
| Sodium tripolyphosphate | 25 |
| Sodium sulphate | 7 |
| Sodium silicate (SiO$_2$:Na$_2$O = 2:1) | 6 |
| Sodium carboxymethyl cellulose | 1 |
| Sodium ethylene diamine tetraacetic acid | 0.5 |
| Calcium bentonite clay | 2.5 |
| Other heat stable minor ingredients | 3 |
| Water | 38 |
|  | 100 |

The aqueous slurry is then spray dried by a conventional technique to produce detergent granules containing about 10% moisture.

Additional detergent composition components including the deodorant composition and bleaches and bleach activators are then mixed with the spray dried detergent granules.

In a typical example, the finished product has the following composition:

|  | % w/w |
|---|---|
| Spray dried detergent granules | 68.5 |
| Deodorant composition | 0.2 |
| Sodium perborate (bleach) | 30.0 |

Solid products in the form of a bar or tablet can be prepared by first mixing together the heat stable, non-volatile materials and then adding heat labile volatile materials, such as the deodorant composition at a later stage in the process, preferably shortly before extruding and stamping.

Use of Deodorant Detergent Composition

The deodorant detergent product can be employed in a normal domestic or other laundry processes conveniently employing a washing machine. It is intended that the product is effective both in removing soil from fabrics being washed and in delivering to the fabric a deodorant effective amount of the deodorant composition. A 'deodorant effective amount' of the deodorant composition is defined as sufficient of the composition to reduce body malodour (as measured by the Deodorant Value Test) when the fabric, in the form of a shirt to be worn in contact with the skin, has been subjected to a laundry washing process employing the deodorant detergent product.

For most purposes, the product can be employed at a concentration of 0.05 to 5% by weight of the wash liquor. Preferably, the concentration in the wash is from 0.2 to 2%, most preferably from 0.3 to 1% by weight of the wash liquor.

EXAMPLES OF THE INVENTION

The invention is illustrated by the following examples which exemplify granular soap powders suitable for use as fabric washing products.

EXAMPLE 1

A spray dried granular soap powder was prepared according to the method described herein, the bleach and deodorant composition being mixed with the base after spray drying. The test product had the following composition:

|  | % w/w |
|---|---|
| Anhydrous soap (80:20 tallow:coconut) | 40 |
| Anhydrous sodium silicate (SiO$_2$:Na$_2$O = 2.5:1) | 8 |
| Magnesium sulphate | 0.5 |
| Sodium EDTA | 0.15 |
| Sodium perborate | 30 |
| Sodium tripolyphosphate | 8 |
| Sodium carboxymethyl cellulose | 0.5 |
| Sodium carbonate | 2.0 |
| Deodorant composition 1 | 0.2 |
| Moisture and minor ingredients to | 100 |

The control product had a similar composition except that the deodorant composition was omitted.

The deodorant composition employed in the test product had the following formulation:

| Deodorant Composition 1 | | | |
|---|---|---|---|
|  | Parts | Class | Total in class |
| Components |  |  |  |
| iso-Amyl salicylate | 5.0 | 1 |  |
| Benzyl salicylate | 4.0 | 1 | 10.25 |
| LRG 201 | 1.25 | 1 |  |
| Bergamot AB 430 | 15.0 | 2 |  |
| Geranium AB 76 | 4.0 | 2 | 20.7 |
| Opoponax resinoid | 1.7 | 2 |  |
| 1,3,4,6,7,8-Hexahydro-4,6,6,7,-8,-hexamethylcyclopenta-γ-2-benzopyran | 10.0 | 4 | 10.0 |
| o-t-Butylcyclohexyl acetate | 0.5 | 5 |  |
| Diethyl phthalate | 3.75 | 5 | 4.25 |
| Nonanolide-1,4 | 0.2* | (5) |  |
| Ingredients |  |  |  |
| Amber AB 358 | 3.0 |  |  |
| Benzyl alcohol | 0.15 |  |  |
| Cedar atlas oil | 5.0 |  |  |
| Citronellol | 7.0 |  |  |
| Citronella oil | 16.1 |  |  |
| Citronellyloxyacetaldehyde | 0.5 |  |  |
| Hexyl aldone | 0.7 |  |  |
| Jasmin AB 284 | 12.0 |  |  |
| Orange oil sweet | 8.0 |  |  |
| 10-Undecen-1-al | 0.15 |  |  |
| Vetyvert oil | 2.0 |  |  |
|  | 100.0 |  |  |
| Total amount of components | 45.2 |  |  |
| Number of components present | 9 |  |  |
| Average amount of each component | 5.0 |  |  |

-continued

| Deodorant Composition 1 | | | |
|---|---|---|---|
| | Parts | Class | Total in class |
| Number of classes represented | 4 | | |

*eliminated from calculation - below threshold value of 0.5%

In this example, the effect of a deodorant composition incorporated in a fabric washing soap powder was evaluated by the Deodorant Value Test referred to above but modified in the following manner.

Polyester cotton coat style button through shirts were first prewashed in an automatic washing machine using a nonionic detergent fabric washing powder. This was to ensure that the shirts to be used in the test were all equally clean and free from dressing prior to washing in the deodorant fabric washing product.

The washed shirts were line dried and then washed again in the automatic washing machine. The test fabric washing soap product was then added to the wash liquor at a concentration of 0.4% by weight of the liquor. The ratio of shirt fabric (dry weight basis) to wash liquor was 40 g fabric per liter wash liquor.

The shirts were agitated in the wash liquor for 10 minutes at a temperature of 50° C., then rinsed and spun to a moisture content of about 50% water and finally line dried to a moisture content of not greater than 10%.

A further batch of prewashed shirts which were to serve as control shirts were washed again and then dried under similar conditions except that deodorant composition was omitted from the fabric washing product added to the wash liquor.

The shirts were folded and stored overnight in polyethylene bags until required for testing by a panel of male subjects and assessing for odour by a panel of female assessors.

The above procedure was repeated on four consecutive days without prewashing, half of the subjects wearing shirts treated with the deodorant composition-containing detergent product and half wearing control shirts without deodorant composition treatment.

Body odour transferred to the shirts in the region of the axillae was assessed by the trained female assessors in the manner described in the Deodorant Value Test, the odour of the shirt fabric being scored in each case rather than the axillae of the panel subjects.

| Results of Deodorant Value Test 1 using soap powder | | |
|---|---|---|
| | Control powder | Test powder |
| Average scores | 2.54 | 1.98 |
| Deodorant value | | 0.56 |

By way of comparison, the Deodorant Value of the Deodorant Composition 1 was also determined in the standard 80/20/5 soap base as described in the Deodorant Value Test.

| Results of Deodorant Value Test 1 using 80/20/5 soap base bar | | |
|---|---|---|
| | Control bar | Test bar |
| Average scores | 3.46 | 2.93 |
| Deodorant value | | 0.53 |

EXAMPLE 2

In this example the effect of a deodorant composition incorporated in a non-soap detergent (NSD)-soap fabric washing powder was evaluated by the Deodorant Value Test referred to above.

The powder had the following formulation:

| | % w/w |
|---|---|
| Sodium $C_{13-18}$ alkane sulphonate | 8.0 |
| $C_{12-20}$ n-alcohol + 25 moles ethylene oxide | 3.4 |
| Sodium soap (containing 4 parts tallow fatty acid to 1 part coconut fatty acid) | 3.4 |
| Pentasodium tripolyphosphate | 37.3 |
| Sodium sulphate | 6.7 |
| Carboxymethylcellulose | 2.0 |
| Ethylene diamine tetraacetic acid | 1.0 |
| Magnesium silicate | 2.0 |
| Fluorescer | 0.3 |
| Waterglass powder ($Na_2O:SiO_2$ = 1:3.4) | 5.9 |
| Sodium carbonate | 1.0 |
| Sodium perborate monohydrate | 19.0 |
| Water | 10.0 |

This product was employed as the control product, while a corresponding test product was prepared by adding to the formulation 0.2% by weight of deodorant composition 2 which had the following composition:

| Deodorant Composition 2 | | | |
|---|---|---|---|
| | Parts | Class | Total in class |
| Components | | | |
| Carvacrol | 3.5 | 1 | 4.5 |
| Thyme oil red | 1.0 | 1 | |
| Bergamot AB 37 | 20.0 | 2 | |
| Pomeransol AB 413 | 6.0 | 2 | 30.0 |
| Petitgrain oil | 4.0 | 2 | |
| 6-Acetyl-1,1,3,4,4,6-hexamethyl-tetrahydro-naphthalene | 3.0 | 3 | 8.0 |
| β-Methyl naphthyl ketone | 5.0 | 3 | |
| 3a-Methyl-dodecahydro-6,6,9a-trimethyl naphtho-2(2,1-b) furan | 0.25* | (4) | |
| β-Naphthol methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |
| Lime AB 402 | 10.0 | | |
| Lavendin oil | 4.0 | | |
| l-Menthol | 8.0 | | |
| Neroli AB 78 | 6.0 | | |
| Orange oil sweet | 5.0 | | |
| | 100.0 | | |
| Total amount of components | 51.5 | | |
| Number of components present | 8 | | |
| Average amount of each component | 6.4 | | |
| Number of classes represented | 4 | | |

*eliminated from calculation - below threshold value of 0.5%

| Results of Deodorant Value Test 2 using NSD/soap powder | | |
|---|---|---|
| | Control bar | Test bar |
| Average scores | 2.72 | 1.26 |
| Deodorant value | | 1.46 |

By way of comparison, the Deodorant Value of Deodorant Composition 2 was also determined in the standard 80/20/5 soap base as described in the Deodorant Value Test.

| Results of Deodorant Value Test 2 using 80/20/5 soap base bar | | |
|---|---|---|
| | Control bar | Test bar |
| Average scores | 3.34 | 2.73 |
| Deodorant value | | 0.61 |

EXAMPLE 3

In this example, the effect of a deodorant composition incorporated in a non-soap detergent (NSD)/soap powder was evaluated by the Deodorant Value Test referred to above.

The powder had the following formulation:

| | % w/w |
|---|---|
| Sodium dodecyl benzene sulphonate | 15 |
| Tallow alcohol 18 EO ⎱ nonionic detergent | 3 |
| Tallow alcohol 12 EO ⎰ | 3 |
| Sodium stearate (soap) | 6 |
| Sodium tripolyphosphate | 40 |
| Sodium silicate | 5 |
| Sodium carboxymethylcellulose | 2 |
| Fluorescer | 0.2 |
| EDTA | 0.2 |
| Enzyme | 0.66 |
| Sodium sulphate | 14 |
| Water | to 100 |

This product was employed as the control product, while a corresponding test product was prepared by adding to the formulation 0.2% by weight of deodorant composition 3 which had the following composition:

| Deodorant Composition 3 | | | |
|---|---|---|---|
| | Parts | Class | Total in class |
| Components | | | |
| Mousse de chene Yugo | 1.25 | 1 | ⎫ 11.25 |
| Pimento leaf oil | 10.0 | 1 | ⎭ |
| Benzoin Siam resinoids | 5.0 | 2 | ⎫ |
| Bergamot AB 430 | 15.0 | 2 | ⎬ 25.0 |
| Geranium oil | 5.0 | 2 | ⎭ |
| p-t-Amylcyclohexanone | 5.0 | 3 | ⎫ 17.0 |
| α-iso-Methyl ionone | 12.0 | 3 | ⎭ |
| Coumarin | 4.0 | 4 | ⎫ |
| 1,3,4,6,7,8-Hexahydro-4,6,6,7,8,8-hexamethyl-cyclopenta-α-2-benzopyran | 3.0 | 4 | ⎬ 7.0 |
| Diethyl phthalate | 4.35 | 5 | 4.35 |
| Ingredients | | | |
| Hercolyn D | 12.25 | | |
| Lavendin oil | 10.0 | | |
| Musk ambrette | 3.0 | | |
| Rosenta AB 380 | 10.0 | | |
| Rose-D-oxide | 0.15 | | |
| | 100.0 | | |
| Total amount of components | 64.6 | | |
| Number of components present | 10 | | |
| Average amount of each component | 6.5 | | |
| Number of classes represented | 5 | | |

| Results of Deodorant Value Test 3 using NSD/soap powder | | |
|---|---|---|
| | Control bar | Test bar |
| Average scores | 2.68 | 1.68 |
| Deodorant value | | 1.00 |

By way of comparison, the Deodorant Value of the Deodorant Composition 3 was also determined in the standard 80/20/5 soap base as described in the Deodorant Value Test.

| Results of Deodorant Value Test 3 using 80/20/5 soap base bar | | |
|---|---|---|
| | Control bar | Test bar |
| Average scores | 3.04 | 2.47 |
| Deodorant value | | 0.57 |

EXAMPLES 4 TO 12

Examples 1 to 3 can be repeated by employing any of the soap powder formulations disclosed herein with any of the following deodorant compositions:

| Deodorant Composition 4 | | | |
|---|---|---|---|
| | Parts | Class | Total in class |
| Components | | | |
| Ethyl vanillin | 0.2* | (1) | |
| iso-Eugenol | 5.0 | 1 | ⎫ 6.25 |
| LRG 201 | 1.25 | 1 | ⎭ |
| Bergamot AB 430 | 8.0 | 2 | ⎫ 15.0 |
| Patchouli oil | 7.0 | 2 | ⎭ |
| 2-n-Heptylcyclopentanone | 0.5 | 3 | ⎫ 5.5 |
| α-iso-Methyl ionone | 5.0 | 3 | ⎭ |
| β-Naphthol methylether | 7.5 | 4 | 7.5 |
| p-t-Butylcyclohexyl acetate | 4.3 | 5 | ⎫ |
| Diethyl phthalate | 8.25 | 5 | ⎬ |
| i-Nonyl formate | 5.0 | 5 | ⎬ 26.55 |
| Nonanediol-1,3-diacetate | 4.0 | 5 | ⎬ |
| Phenylethyl phenyl acetate | 5.0 | 5 | ⎭ |
| Tetrahydro muguol | 6.0 | 6 | 6.0 |
| Ingredients | | | |
| Citronella oil | 6.0 | | |
| Green Herbal AB 502 | 15.0 | | |
| Indole | 1.5 | | |
| Rosenta AB 380 | 6.0 | | |
| Sandalone | 4.0 | | |
| α-Undecalactone | 0.5 | | |
| | 100.0 | | |
| Total amount of components | 66.8 | | |
| Number of components present | 14 | | |
| Average amount of each component | 4.8 | | |
| Number of classes represented | 6 | | |

*eliminated from calculation - below threshold value of 0.5%

| Deodorant Composition 5 | | | |
|---|---|---|---|
| | Parts | Class | Total in class |
| Components | | | |
| Benzyl salicylate | 15.0 | 1 | ⎫ 21.0 |
| Mousse de chene Yugo | 6.0 | 1 | ⎭ |
| Bergamot AB 430 | 15.0 | 2 | 15.0 |
| 6-Acetyl-1,3,4,4,4,6-hexamethyl tetrahydronaphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b) | | | |

Deodorant Composition 5

| | Parts | Class | Total in class |
|---|---|---|---|
| furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |
| Trichloromethyl phenyl carbinyl acetate | 0.2 | | |
| | 100.0 | | |
| Total amount of components | | | 63.29 |
| Number of components present | | | 7 |
| Average amount of each component | | | 9.0 |
| Number of classes represented | | | 6 |

*eliminated from calculation - below threshold value for a component of 0.5%

Deodorant Composition 6

| | Parts | Class | Total in class |
|---|---|---|---|
| Components | | | |
| Clove leaf oil | 10.0 | 1 | 11.25 |
| LRG 201 | 1.25 | 1 | |
| Petitgrain oil | 10.0 | 2 | 10.0 |
| p-t-Butyl-α-methyl hydro cinnamic aldehyde | 15.0 | 3 | 15.0 |
| 3a-Methyl-dodecahydro-6,6,9a-trimethylnaphtho-2(2,1-b) furan | 0.5 | 4 | 0.5 |
| o-t-Butylcyclohexyl acetate | 2.0 | 5 | 21.25 |
| Diethyl phthalate | 9.25 | 5 | |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |
| Total amount of components | | | 68.0 |
| Number of components present | | | 9 |
| Average amount of each component | | | 7.6 |
| Number of classes represented | | | 6 |

| Dimyrcetol | Dimyrcetol (IFF) |
|---|---|
| Hercolyn D | Tetrahydro abietate + dihydro abietate (HP) |
| LRG 201 | Oakmoss speciality (RB) |
| Pelargene | Pelargene (PPL) |
| Rose-D-Oxide | Rose oxide synthetic (PPL) |
| Sandalone | Sandalone (PPL) |
| Perfume Houses | |
| HP | Hercules Powder Co. |
| IFF | International Flavour & Fragrences Inc. |
| RB | Roure Bertrand |
| PPL | Proprietary Perfumes Limited |

All materials which are classified by a name and number, such as those having the 'AB' notation, are obtainable from Properietary Perfumes Limited.

What is claimed is:

1. A deodorant detergent product comprising:
   (i) from 1 to 99% by weight of a soap;
   (ii) from 0.99 to 98.99% by weight of other detergent adjuncts including at least one selected from the group consisting of detergency builders (other than soap) and bleaches; and
   (iii) from 0.01 to 10% by weight of a deodorant composition comprising from 45 to 100% by weight of deodorant active components, said components having a lipoxidase-inhibiting capacity of at least 50% or a Raoult variance ratio of at least 1.1, said components being classified into six classes consisting of:
   Class 1: phenolic substances
   Class 2: essential oils, extracts, resins and synthetic oils
   Class 3: aldehydes and ketones
   Class 4: polycyclic compounds
   Class 5: esters
   Class 6: alcohols,
   provided that where a component can be classified into more than one class, it is placed in the lower or lowest numbered class;
   said components being so selected that
   (a) the deodorant composition contains at least five components of which at least one must be selected from each of Class 1, Class 2 and Class 4;
   (b) the deodorant composition contains components from at least 4 of the 6 classes; and
   (c) any component present in the deodorant composition at a concentration of less than 0.5% by weight of said composition is eliminated from the requirements of (a) and (b)
   said deodorant composition having a deodorant value of from 0.50 to 3.5 as measured by the Deodorant Value Test.

2. The deodorant detergent product of claim 1 wherein the deodorant composition has a deodorant value of from 0.90 to 3.5 as measured by the Deodorant Value Test.

3. The deodorant detergent product of claim 1 wherein the deodorant composition has a deodorant value of from 1.20 to 3.5 as measured by the Deodorant Value Test.

4. The deodorant detergent product of claim 1 wherein the builder is an inorganic phosphate.

5. The deodorant detergent product of claim 1 wherein the builder is an alkali metal salt selected from the group consisting of carbonates, bicarbonates, borates and silicates.

6. The deodorant detergent product of claim 1 wherein the bleach is a perborate or a percarbonate.

7. The deodorant detergent product of claim 1 further comprising a non-soap detergent active compound selected from the group consisting of anionic, nonionic, cationic, amphoteric and zwitterionic detergent active compounds.

8. The deodorant detergent product of claim 1 wherein the amount of deodorant components present in said class comprising phenolic substances and said class comprising essential oils, extracts, resins and synthetic oils and said class comprising polycyclic compounds, is at least 1% by weight of the deodorant composition for each of said classes, and the amount of perfume components present in said further class chosen from the remaining three classes is at least 1% by weight of the deodorant composition.

9. The deodorant detergent product of claim 1 wherein the average concentration of all such components present is at least 5% by weight where four of said classes is represented, or at least 4.5% by weight where five or six of said classes is represented.

10. The deodorant detergent product of claim 1 wherein the amount of deodorant components present in said class comprising phenolic substances and said class comprising essential oils, extracts, resins and synthetic oils and said class comprising polycyclic compounds, is at least 3% by weight of the deodorant composition for each of said classes and the amount of deodorant components present in said further class chosen from the remaining three classes is at least 3% by weight of the deodorant composition.

11. The deodorant detergent product of claim 1 wherein at least five of the classes are represented.

12. The deodorant detergent product of claim 1 wherein all six classes are represented.

13. A process for preparing the deodorant detergent product of claim 1 which comprises mixing the soap and detergent adjuncts, including at least one selected from the group consisting of detergency builders (other than soap) and bleaches, with the deodorant composition to provide said product comprising from 1 to 99% by weight of said soap, from 0.99 to 98.99% by weight of said detergent builder and 0.01 to 10% by weight of said deodorant composition.

14. A method for suppressing human body malodour, which comprises contacting the skin in the region of apocrine sweat glands with a fabric treated with the deodorant detergent product of claim 1.

* * * * *